United States Patent [19]

Masuda

[11] Patent Number: 5,700,234
[45] Date of Patent: Dec. 23, 1997

[54] MAGNETIC THERAPEUTIC APPARATUS

[75] Inventor: Isamu Masuda, Fukuoka, Japan

[73] Assignee: Nihon Kenko Zoushin Kenkyukai Corporation, Fukuoka, Japan

[21] Appl. No.: 505,358
[22] PCT Filed: Feb. 7, 1994
[86] PCT No.: PCT/JP94/00183
§ 371 Date: Aug. 30, 1995
§ 102(e) Date: Aug. 30, 1995
[87] PCT Pub. No.: WO95/20994
PCT Pub. Date: Aug. 10, 1995
[51] Int. Cl.$^6$ ..................................................... A61N 1/00
[52] U.S. Cl. ........................................................ 600/15
[58] Field of Search ..................... 600/9–15; 128/597–98

[56] References Cited

U.S. PATENT DOCUMENTS 4,850,340  7/1989  Onishi ........................................ 600/13
5,344,384  9/1994  Ostrow et al. ............................. 600/13

FOREIGN PATENT DOCUMENTS 50-121997  10/1975  Japan .
54-38815   3/1979   Japan .
61-159941  10/1986  Japan .

*Primary Examiner*—John P. Lacyk
*Attorney, Agent, or Firm*—Jordan and Hamburg

[57] ABSTRACT

A magnetic therapeutic apparatus comprising a plurality of magnetic therapeutic units (4A)(4B) including one or more electromagnetic solenoids (17) as magnetic field generating source, and a timer (1) which is disposed between the magnetic therapeutic units (4A)(4B) and an AC power source and controls the operation time of the magnetic therapeutic units (4A)(4B) all at once. The magnetic therapeutic units (4A)(4B) are respectively connected with electric cord wires (5A)(5B) provided with plugs (10A)(10B) at the ends thereof, and the timer (1) is provided with a plurality of plug-in sockets (6A)(6B) which can respectively be connected with the plugs (10A)(10B).

The plugs (10A)(10B) of the electric cord wires (5A)(5B) are respectively inserted into the plug-in sockets (10A)(10B), which makes it possible to set the time for respective magnetic therapeutic units (4A)(4B) by one timer (1), so time setting operation for magnetic therapeutic units (4A)(4B) becomes easy.

2 Claims, 5 Drawing Sheets

MAGNETIC THERAPEUTIC APPARATUS

BACKGROUND OF THE INVENTION

The present invention relates to a combination of a timer and magnetic therapeutic units, each having electromagnetic solenoids as a generating source of a magnetic field, and more particularly to a magnetic therapeutic apparatus which can set operation time of a plurality of magnetic therapeutic units arbitrarily by one timer.

The applicant of the present invention has previously proposed a magnetic therapeutic unit having a configuration that a plurality of case bodies including electromagnetic solenoids therein are flexibly connected with each other in series with their magnetic pole faces directing in a common direction. When an AC current flows through the electromagnetic solenoids in the case bodies, after fastening the magnetic therapeutic unit around affected portions of a body, alternating magnetic fields generated in the electromagnetic solenoids act on the body, thereby such symptoms as stiffness are cured.

This kind of magnetic therapeutic unit is designed to generate vibration and heat by energizing the electromagnetic solenoid, thereby, in addition to the above-mentioned magnetic therapeutic effect, massaging and warming effects are exerted on the body. Moreover, it has been experimentally proved that, when the magnetic therapeutic unit is used while sleeping, the mutual action of warming and vibration facilitates the sleeping.

Usually, the magnetic therapeutic unit is connected to an AC power source through a timer in use. When setting an operation time by the timer, the magnetic therapeutic unit operates for the set time and then stops.

An electric cord wire provided with a plug at its tip is drawn out from the magnetic therapeutic unit, while a plug-in socket is provided on the timer so as to be connected to the plug fixed to the electric cord wire. The plug of the magnetic therapeutic unit includes a pair of parallel connecting plates, while the timer socket includes a pair of connecting holes which can engage with and disengage from the connecting plates of the plug.

When the affected portions such as stiffened portions extend to plural locations, one magnetic therapeutic unit is used by fastening to plural portions in turn, but if a plural number of the magnetic therapeutic units are prepared, each being fastened to the affected portions, all of the affected portions can be treated simultaneously by operating all the magnetic therapeutic units at once.

However, in the case of using the plural number of magnetic therapeutic units, it is necessary to set the timers of the units separately, causing setting operations to be complicated.

Furthermore, since the plug of the magnetic therapeutic unit so constructed that a pair of connecting plates are projected in parallel, and, the timer socket has a pair of connecting holes in parallel for accepting the connecting plates of the plug, mechanical resistance against an external force perpendicular to the face of the connecting plates is weak. Therefore, the connecting plates may be extracted from the connecting holes and the plug may be extracted by a small vibration in a specific direction.

Additionally, since it is possible to connect any of the plugs of other equipment to this timer socket, the timer may be employed for the other equipment, and as a result, the timer may be damaged by an overcurrent.

SUMMARY OF THE INVENTION

It is a first object of the present invention to provide a magnetic therapeutic apparatus, wherein the time setting operation for a plural number of magnetic therapeutic units is simplified by connecting the plural number of magnetic therapeutic units to one timer.

It is a second object of the present invention to provide a magnetic therapeutic apparatus, wherein by devising respective directions of the metal plates of a plug of an electric cord wire connected to each magnetic therapeutic unit and the connecting holes of a plug-in socket provided on the timer, an engagement force of the plug is increased, disengagement of the plug from the socket is prevented and the timer can not be applied to the other equipments.

In order to achieve the first object, in the present invention, a magnetic therapeutic apparatus comprises a plurality of magnetic therapeutic units including electromagnetic solenoids as magnetic field generating source, and a timer disposed between the magnetic therapeutic units and an AC power source to control the operation time of the all magnetic therapeutic units at once. Each magnetic therapeutic unit is equipped with an electric cord wire provided with a plug at the end thereof, and the timer is equipped with a plurality of plug-in sockets to which the plugs are fixed so that the electric cord wires of the magnetic therapeutic units can be connected respectively. According to this configuration, since the plugs of the electric cord wires are respectively inserted into the connecting holes of the timer sockets to connect the magnetic therapeutic units to the timer, it is possible to set the operation time for a plurality of magnetic therapeutic units using one timer, which simplifies time setting.

In order to achieve the second object, in the present invention, a magnetic therapeutic apparatus is proposed, comprising the above-mentioned configuration, and furthermore, a pair of connecting plates projected from each plug of the magnetic therapeutic units so that the directions of the faces of the plates intersect one another at right angles, and a pair of connecting holes to which the connecting plates of said plugs are engageable being so formed in each plug-in socket of the timer that the directions of the openings intersect one another at right angles with respect to the directions of the respective connecting plates. According to this configuration, since respective connecting plates of the plugs are so disposed that the directions of the faces of the plates intersect one another at right angles, even when the external force is exerted perpendicularly on the face of one connecting plate, the direction of the external force and the face of the other connecting plate are in parallel, so a large retaining force is obtained. Moreover, the connecting plates are not extracted from the connecting holes by a small vibration in a specific direction. Furthermore, since respective connecting holes of the plug-in sockets are so formed that the directions of the openings intersect one another at right angles to be adapted to the direction of the connecting plates of the plugs, a general plug having connecting plates disposed in parallel can not be inserted into this plug-in socket, thus the timer can not be applied to other equipment.

DETAILED DESCRIPTION OF THE INVENTION

Figure 1:
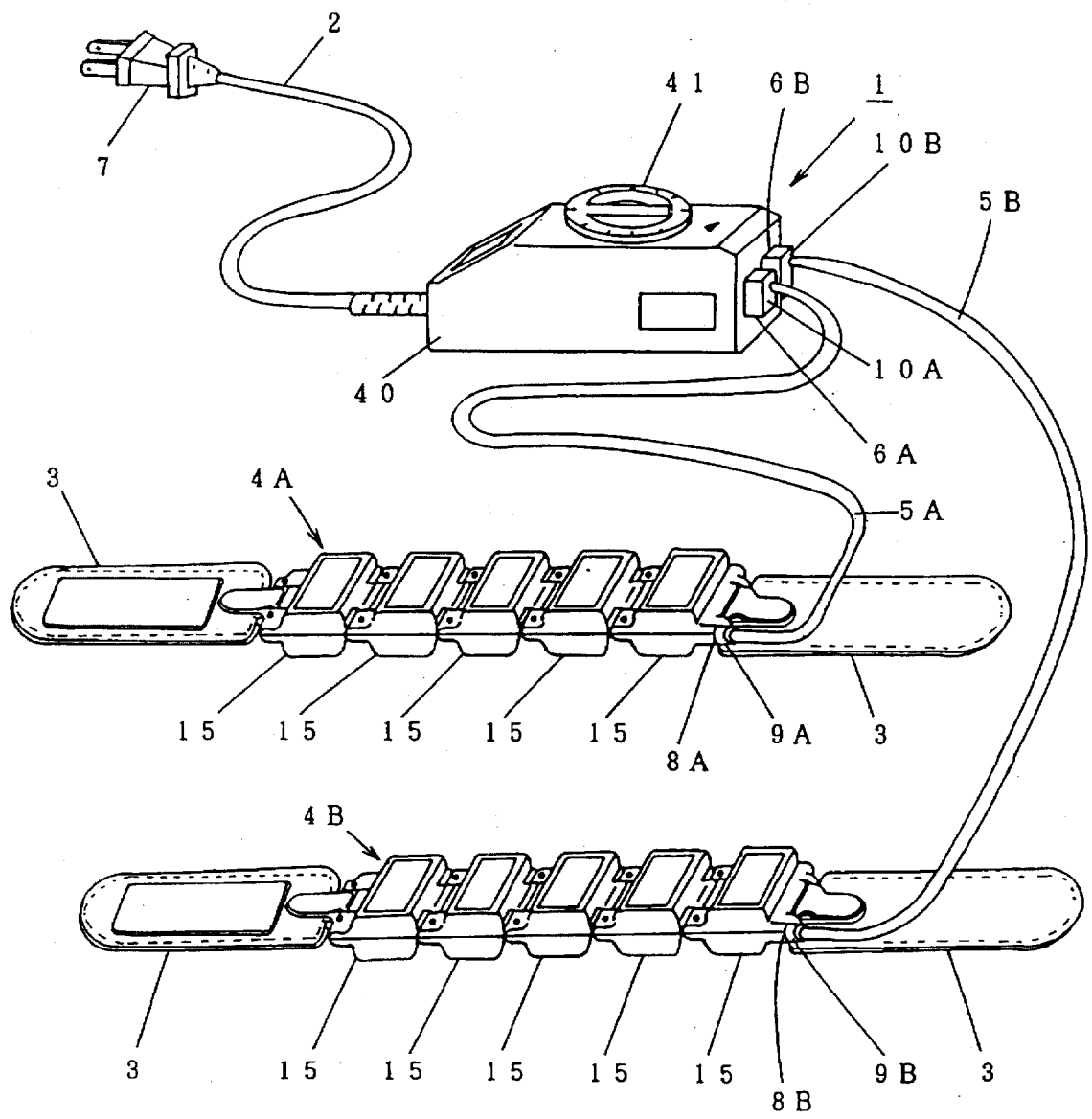
FIG. 1 is a perspective view showing an entire configuration of a magnetic therapeutic apparatus according to one embodiment of the present invention.

FIG. 1 shows an entire configuration of a magnetic therapeutic apparatus according to one embodiment of the present invention, which includes by a plural number (2 units in this embodiment) of magnetic therapeutic units 4A, 4B and a timer 1 for controlling the operation time of all the magnetic therapeutic units 4A, 4B at once.

Each of the magnetic therapeutic units 4A, 4B includes a plural number (5 units in this embodiment) of magnetic field generators 15 which are flexibly connected in one direction. The magnetic therapeutic units 4A, 4B are wound around suitable portions of the body and fixed thereon by connecting fastening belts 3, 3 at the opposite ends.

Figure 4:
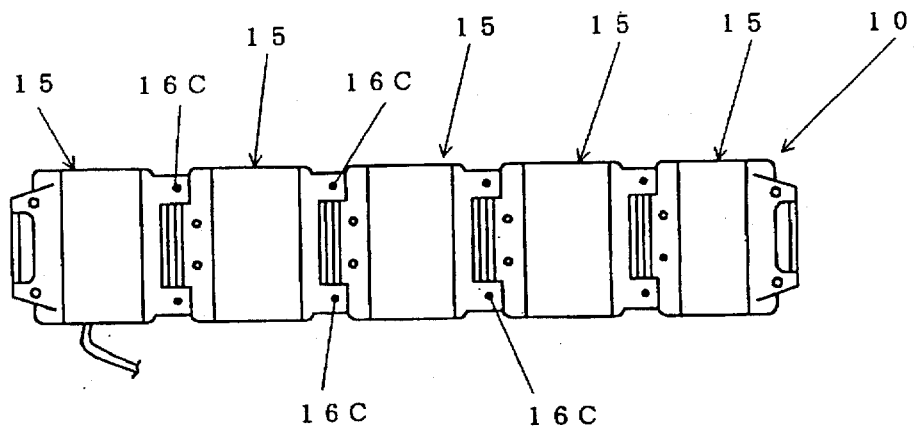
FIG. 4 is a front view of a magnetic therapeutic unit.
Figure 5:
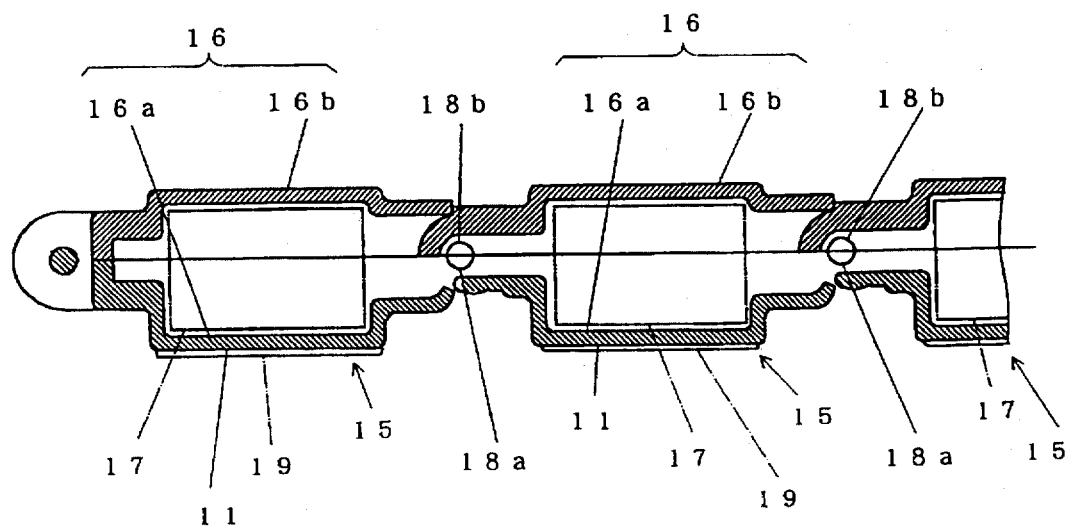
FIG. 5 is a longitudinal sectional view of a magnetic therapeutic unit.

As shown in FIG. 4 and FIG. 5, each magnetic field generator 15 is assembled by disposing an electromagnetic solenoid 17 in a case 16 made of synthetic resin. The case 16 is formed by a pair of partial cases 16a, 16b, whose opening faces are butted against each other and fixed at plural locations by screws 16c. On side end faces of the case 16, either pivots 18a, 18a or bearing holes 18b, 18b widthwise of the case 16 are formed, and by engaging the pivots 18a to the respective bearing holes 18b between the adjoining cases 16, 16, both cases are coupled one another pivotally.

Figure 6:
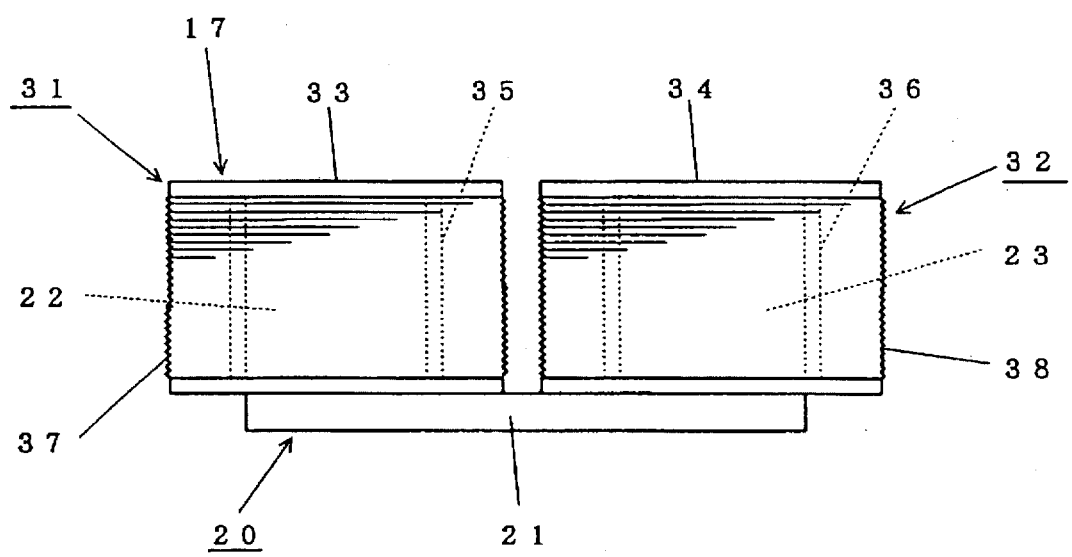
FIG. 6 is a front view showing a configuration of an electromagnetic solenoid.

As shown in FIG. 6, the electromagnetic solenoid 17 includes a laminated iron core 20 including divided portions 22, 23 at the opposite ends of a base 21, and coil bobbins 31, 32 engaged to the divided portions 22, 23. The coil bobbins 31, 32 are formed by winding coils 37, 38 around spools 35, 36 made of synthetic resin and having collars 33, 34 at the opposite ends. When an AC current is flowed through the coils 37, 38, alternating magnetic fields are generated from the end of the divided portions 22, 23.

The electromagnetic solenoids 17 are fixed inside the case 16 with the end faces of the divided portions 22, 23 directed to the one partial case 16a, thereby an external face of said partial case 16a serves as a magnetic pole face 11 which generates magnetic fields.

The magnetic therapeutic units 4A, 4B having the above-mentioned configuration are connected to the timer 1 by electric cord wires 5A, 5B.

At first ends of the electric cord wires 5A, 5B, first plugs 9A, 9B connected to plug-in sockets 8A, 8B provided on the magnetic therapeutic units 4A, 4B are disposed, and at the other ends, second plugs 10A, 10B connected to plug-in sockets 6A, 6B, to be described later in detail, provided on the timer 1 are disposed.

Figure 3:
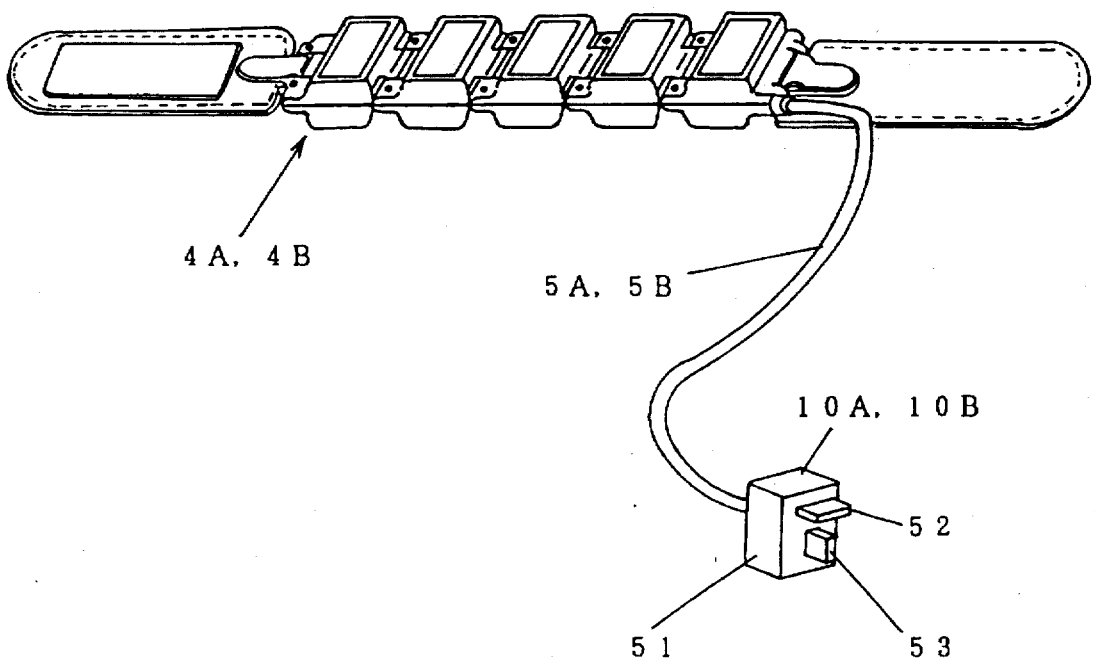
FIG. 3 is a perspective view of a magnetic therapeutic unit and a plug.

As shown in FIG. 3, the second plugs 10A, 10B respectively include a pair of connecting plates 52, 53 projecting on an end face of a plug body 51 made of synthetic resin. The connecting plates 52, 53 are formed with rectangular metal plates, and are so disposed that the directions of the faces of the plates intersect one another at right angles.

In this embodiment, though a T-shaped arrangement is employed by positioning the connecting plate 53 directing lengthwise on a center line of the connecting plate 52 directing widthwise, it is not always restricted thereto, an opposite L-shaped arrangement may be employed by positioning the connecting plate 53 lengthwise near one end portion of the connecting plate 52 oriented widthwise.

The timer 1 is designed to control the operation time of the all magnetic therapeutic units 4A, 4B at once, by disposing between the magnetic therapeutic units 4A, 4B and the AC power source. Though various types of timer may be used as the timer 1, in this embodiment, a mechanical timer incorporating a mechanical timing mechanism and contact mechanism is used.

The above-mentioned mechanisms are built inside a case body 40 made of synthetic resin, and on the upper surface thereof, a time setting knob 41 for arbitrarily setting operation time of the magnetic therapeutic units 4A, 4B is disposed rotatably.

A power cord wire 2 is drawn out from the one end face of the case body 40, and a plug 7 which is to be inserted into an outlet is fixed to the end of the power cord wire 2.

On the other end face of the case body 40, a plural number (2 units in this embodiment) of plug-in sockets 6A, 6B which can be connected to the second plugs 10A, 10B of the electric cord wires 5A, 5B are disposed.

Figure 2:
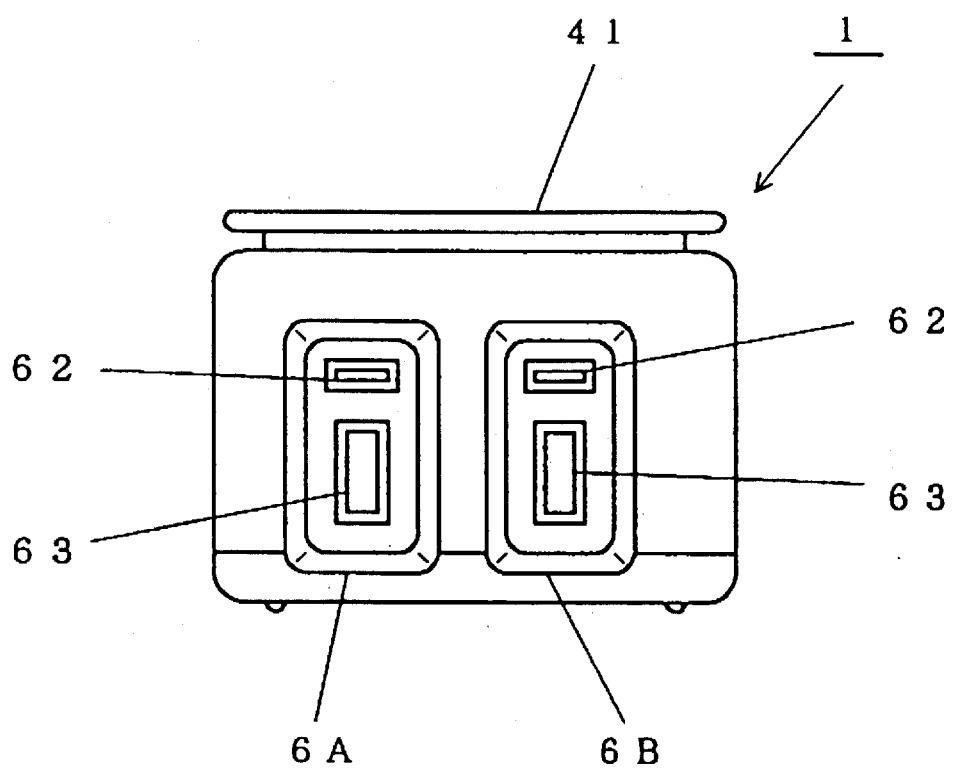
FIG. 2 is a side view of a timer.

As shown in FIG. 2, each of the plug-in sockets 6A, 6B is provided with a pair of rectangular connecting holes 62, 63 which the connecting plates 52, 53 of the plugs 10A, 10B can be inserted into and pulled out from.

The connecting holes 62, 63 are respectively opened at the positions corresponding to the connecting plates 52, 53 of the plugs 10A, 10B, and their rectangular openings are formed in the directions corresponding to the connecting plates 52, 53, in other words, the opening of one connecting hole 62 is formed widthwise and the opening of the other connecting hole 63 is formed lengthwise.

Though not shown, it is to be understood that electrode plates are respectively disposed in the connecting holes 62, 63 for face-contact with the connecting plates 52, 53 inserted therein. The electrode plates are connected in parallel with the power cord wire 2 through a contact mechanism, and when the contact mechanism becomes open after the set time has elapsed, the power supply to the electrode plates is interrupted.

For using the above-mentioned magnetic therapeutic apparatus, after connecting the magnetic therapeutic units 4A, 4B to the timer 1 through the electric cord wires 5A, 5B, the plug 7 of the power cord wire 2 of the timer 1 is inserted into an outlet. Then, the magnetic therapeutic units 4A, 4B are fastened to different portions of the body, and the time setting knob 41 is turned to set a desired operation time. Thereby, the magnetic therapeutic units 4A, 4B are energized to generate the alternating magnetic fields for treatment on respective portions for the set time. When the set time of the timer 1 has elapsed, the magnetic therapeutic units 4A, 4B are cut off current to end the treatment.

In this case, since, at the connections between the electric cord wires 5A, 5B and the timer 1, the connecting plates 52, 53 of the plugs 10A, 10B are so disposed that the directions of the faces thereof intersect one another at right angles, even when an external force is exerted perpendicularly on the face of one connecting plate, the direction of the external force is in parallel to the face of the other connecting plate, so displacement resistance is strong and the connecting plates 52, 53 are not extracted from the connecting holes 62, 63 of the plug-in sockets 6A, 6B, and the plugs 10A, 10B are not extracted by a small vibration in a specific direction.

Also, since the connecting holes 62, 63 of the plug-in sockets 6A, 6B are so formed that the directions of the openings intersect one another at right angles to be adapted to the directions of the connecting plates 52, 53 of the plugs 10A, 10B, a general plug having connecting plates disposed in parallel cannot be inserted into the plug-in sockets 6A, 6B, thus the timer 1 can not be applied to the other equipments, so it is not damaged by an overcurrent.

What is claimed is:

1. A magnetic therapeutic apparatus comprising:

a plurality of magnetic therapeutic units each including one or more electromagnetic solenoids for generating magnetic fields:

a timer unit for applying power to said plurality of magnetic therapeutic units during a selectable time period:

each of said plurality of magnetic therapeutic units having an electric cord with a plug at a distal end thereof for connection to said timer unit: and said timer unit having a plurality of sockets for accepting the plugs of the magnetic therapeutic units.

2. A magnetic therapeutic apparatus according to claim 1 wherein:

each of said plugs have a pair of connecting plates projecting therefrom with planes of said connecting plates substantially perpendicular to each other; and each of said sockets having a pair of connecting slots disposed with planes thereof substantially perpendicular to each other and positioned for accepting the connecting plates of the plugs whereby when said connecting plates are engaged with said connecting slots dislodgement of said plugs from said sockets by forces parallel to said planes of said connecting plates and sockets is prevented.

* * * * *